US00PP22684P2

(12) United States Plant Patent
Schuiver

(10) Patent No.: US PP22,684 P2
(45) Date of Patent: Apr. 24, 2012

(54) ***GERANIUM* PLANT NAMED 'AZURE RUSH'**

(50) Latin Name: ***Geranium wallichianum*×*Geranium himalayense***
Varietal Denomination: Azure Rush

(75) Inventor: Jan Dirk Schuiver, Edewecht/Husbäke (DE)

(73) Assignees: Thomas Waterer, Coventry (GB); Michael Hugo Waterer, Devon, GBX ( * ) Notice: Subject to any disclaimer, the term of this patent is extended or adjusted under 35 U.S.C. 154(b) by 12 days.

(21) Appl. No.: 12/807,252

(22) Filed: Aug. 31, 2010

(51) Int. Cl.
*A01H 5/00* (2006.01)

(52) U.S. Cl. ..... Plt./324

(58) Field of Classification Search ..... Plt./324
See application file for complete search history.

*Primary Examiner* — June Hwu
(74) *Attorney, Agent, or Firm* — C. A. Whealy

(57) ABSTRACT

A new and distinct cultivar of *Geranium* plant named 'Azure Rush', characterized by its compact, upright and outwardly mounding plant habit; moderately vigorous growth habit; deeply dissected leaves; freely and continuous flowering habit; large single light violet-colored flowers with red purple-colored venation; long flowering period; good garden performance; and tolerance to mildew pathogens.

2 Drawing Sheets

Botanical designation: *Geranium wallichianum*×*Geranium himalayense.*

Cultivar denomination: 'AZURE RUSH'.

BACKGROUND OF THE INVENTION

The present invention relates to a new and distinct cultivar of *Geranium* plant, botanically known as *Geranium wallichianum*×*Geranium himalayense,* and hereinafter referred to by the name 'Azure Rush'.

The new *Geranium* plant is a naturally-occurring whole plant mutation of *Geranium wallichianum*×*Geranium himalayense* 'Rozanne', disclosed in U.S. Plant Pat. No. 12,175. The new *Geranium* was discovered and selected by the Inventor as a single flowering plant from within a population of plants of 'Rozanne' in a controlled greenhouse environment in Jeddeloh, Germany in July, 2007.

Asexual reproduction of the new *Geranium* plant by tissue culture in a controlled environment in Bressingham, United Kingdom since February, 2008, has shown that the unique features of this new *Geranium* are stable and reproduced true to type in successive generations.

SUMMARY OF THE INVENTION

Plants of the new *Geranium* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Azure Rush'. These characteristics in combination distinguish 'Azure Rush' as a new and distinct *Geranium* plant:

1. Compact, upright and outwardly mounding plant habit.
2. Moderately vigorous growth habit.
3. Deeply dissected leaves.
4. Freely and continuous flowering habit.
5. Large single light violet-colored flowers with red purple-colored venation.
6. Long flowering period.

7. Good garden performance.
8. Tolerant to mildew pathogens.

Plants of the new *Geranium* differ primarily from plants of the parent, 'Rozanne', in flower color as plants of 'Rozanne' have violet blue-colored flowers with white-colored centers and purple violet-colored venation.

Plants of the new *Geranium* can be compared to plants of *Geranium wallichianum* 'Buxton's Blue', not patented. In side-by-side comparisons conducted in Bressingham, United Kingdom, plants of the new *Geranium* differed primarily from plants of 'Buxton's Blue' in flower color as plants of 'Buxton's Blue' had light pale blue-colored flowers with white-colored centers.

BRIEF DESCRIPTION OF THE PHOTOGRAPHS

The accompanying colored photographs illustrate the overall appearance of the new *Geranium* plant, showing the colors as true as it is reasonably possible to obtain in colored reproductions of this type. Colors in the photographs may differ slightly from the color values cited in the detailed botanical description which accurately describe the colors of the new *Geranium* plant. The photograph on the first sheet comprises a side perspective view of a typical flowering plant of 'Azure Rush' grown in a container.

The photograph on the second sheet is a close-up view of typical flowers of 'Azure Rush'.

DETAILED BOTANICAL DESCRIPTION

The aforementioned photographs and following observations, measurements and values describe plants grown during the summer in four-liter containers in an outdoor nursery in Bressingham, United Kingdom. During the production of the plants, day temperatures averaged 25° C. and night temperatures averaged 15° C. Plants were two years old when the photographs and the description were taken. In the detailed description, color references are made to The Royal Horticultural Society Colour Chart, 1996 Edition, except where general terms of ordinary dictionary significance are used.

Botanical classification: *Geranium wallichianum*×*Geranium himalayense* 'Azure Rush'.

Parentage: Naturally-occurring whole plant mutation of *Geranium wallichianum*×*Geranium himalayense* 'Rozanne', disclosed in U.S. Plant Pat. No. 12,175.

Propagation:

*Type.*—By tissue culture.

*Time to initiate roots, summer.*—About 15 days at 21° C. air temperature.

*Time to initiate roots, winter.*—About 40 days at 21° C. air temperature.

*Time to produce a rooted young plant, summer.*—About 25 days at 21° C. air temperature.

*Time to produce a rooted young plant, winter.*—About 90 days at 5° C. air temperature.

*Root description.*—Medium to thick, fleshy and fibrous; close to 159B in color.

*Rooting habit.*—Moderately freely branching; moderately dense.

Plant description:

*General appearance and habit.*—Hardy herbaceous perennial; compact, upright and outwardly mounding plant habit; clumping and low spreading; moderately vigorous growth habit.

*Plant height, soil level to top of foliar plane.*—About 40 cm.

*Plant height, soil level to top of floral plane.*—About 50 cm.

*Plant width.*—About 70 cm.

Lateral branch description:

*Branching habit.*—Freely basal branching habit; pinching is not required; about eight to twelve lateral branches develop per plant.

*Length.*—About 40 cm.

*Diameter.*—About 6 mm.

*Internode length.*—About 3 cm to 9 cm.

*Strength.*—Strong.

*Aspect.*—Lateral branches grow outwardly to spreading horizontally.

*Texture.*—Pubescent.

*Color.*—Close to 145A.

Foliage description:

*Arrangement.*—Opposite, simple.

*Length.*—About 5 cm.

*Width.*—About 7 cm.

*Shape.*—Deeply palmately incised with five main dissected lobes.

*Apex.*—Acute.

*Base.*—Sagittate.

*Margin.*—Palmately cleft; lobes biserrate and sinuate.

*Venation pattern.*—Palmate; reticulate.

*Texture, upper and lower surfaces.*—Pubescent; rough.

*Color.*—Developing leaves, upper surface: Close to 144B. Developing leaves, lower surface: Close to 144D. Fully developed leaves, upper surface: Close to 137A; venation, close to 137A; during the summer, tinged with close to 144A; during the autumn, tinged with close to 46C. Fully developed leaves, lower surface: Close to 137C; venation, close to 137C.

*Petiole.*—Length: About 8 cm. Diameter: About 4 mm. Texture, upper and lower surfaces: Pubescent. Color, upper and lower surfaces: Close to 145A.

Flower description:

*Flower arrangement/habit.*—Single rotate flowers arranged in axillary cymes; freely flowering habit with usually 15 open flowers and 22 flower buds per inflorescence; flowers face upright to outwardly.

*Fragrance.*—Not detected.

*Flowering season.*—Plants begin flowering about three months after planting; in the garden, flowering is continuous from mid June to first frost in Germany.

*Flower longevity.*—Flowers last about ten days on the plant; corolla not persistent, corona persistent.

*Flower buds.*—Length: About 1 cm. Diameter: About 5 mm. Shape: Ovoid. Color: Close to 145A.

*Flower diameter.*—About 3 cm.

*Flower depth.*—About 5 cm.

*Petals.*—Quantity per flower: Five in a single whorl. Length: About 3 cm. Width: About 2 cm. Shape: Obcordate. Apex: Rounded. Base: Attenuate. Margin: Entire. Texture, upper and lower surfaces: Smooth, glabrous. Color: When opening, upper surface: Close to 84A. When opening, lower surface: Close to 84B; venation, close to 79A. Fully opened, upper surface: Close to 84B; venation, close to 79A; color becoming closer to 84B to 84C with development. Fully opened, lower surface: Close to 84C; venation, close to 79A.

*Sepals.*—Quantity per flower: Five, arranged in a single whorl. Length: About 1 cm. Width: About 5 mm. Shape: Ovate. Apex: Acuminate. Base: Cuneate. Margin: Entire. Texture, upper and lower surfaces: Pubescent. Color, upper surface: Close to 145A. Color, lower surface: Close to 145B.

*Peduncles* (*flower cluster stalk*).—Length: About 5 cm. Diameter: About 3 mm. Strength: Strong. Texture: Pubescent. Color: Close to 145A; tinged with close to 46C in the autumn.

*Pedicels* (*individual flower stalk*).—Length: About 3 cm. Diameter: About 3 mm. Strength: Strong. Texture: Pubescent. Color: Close to 145A; tinged with close to 46C in the autumn.

*Reproductive organs.*—Androecium: Stamen quantity per flower: About ten. Filament length: About 3 mm. Filament color: Close to 79B. Anther length: About 3 mm. Anther shape: Ovate. Anther color: Close to 79B. Pollen amount: None observed. Gynoecium: Pistil quantity per flower: One. Pistil length: About 4 mm. Stigma shape: Five-parted. Stigma color: Close to 79B. Style length: About 4 mm. Style color: Close to 79B. Ovary color: Close to 145A.

*Seed/fruits.*—Seed and fruit development have not been observed.

Disease/pest resistance: Plants of the new *Geranium* have been observed to be tolerant to mildews pathogens. Plants of the new *Geranium* have not been observed to resistant to pests and other pathogens common to *Geraniums*.

Garden performance: Plants of the new *Geranium* have exhibited good garden performance and to tolerate rain and wind, to be hardy to USDA Zones 5 to 8 and to tolerate high temperatures of about 30° C.

It is claimed:

1. A new and distinct *Geranium* plant named 'Azure Rush' as illustrated and described.

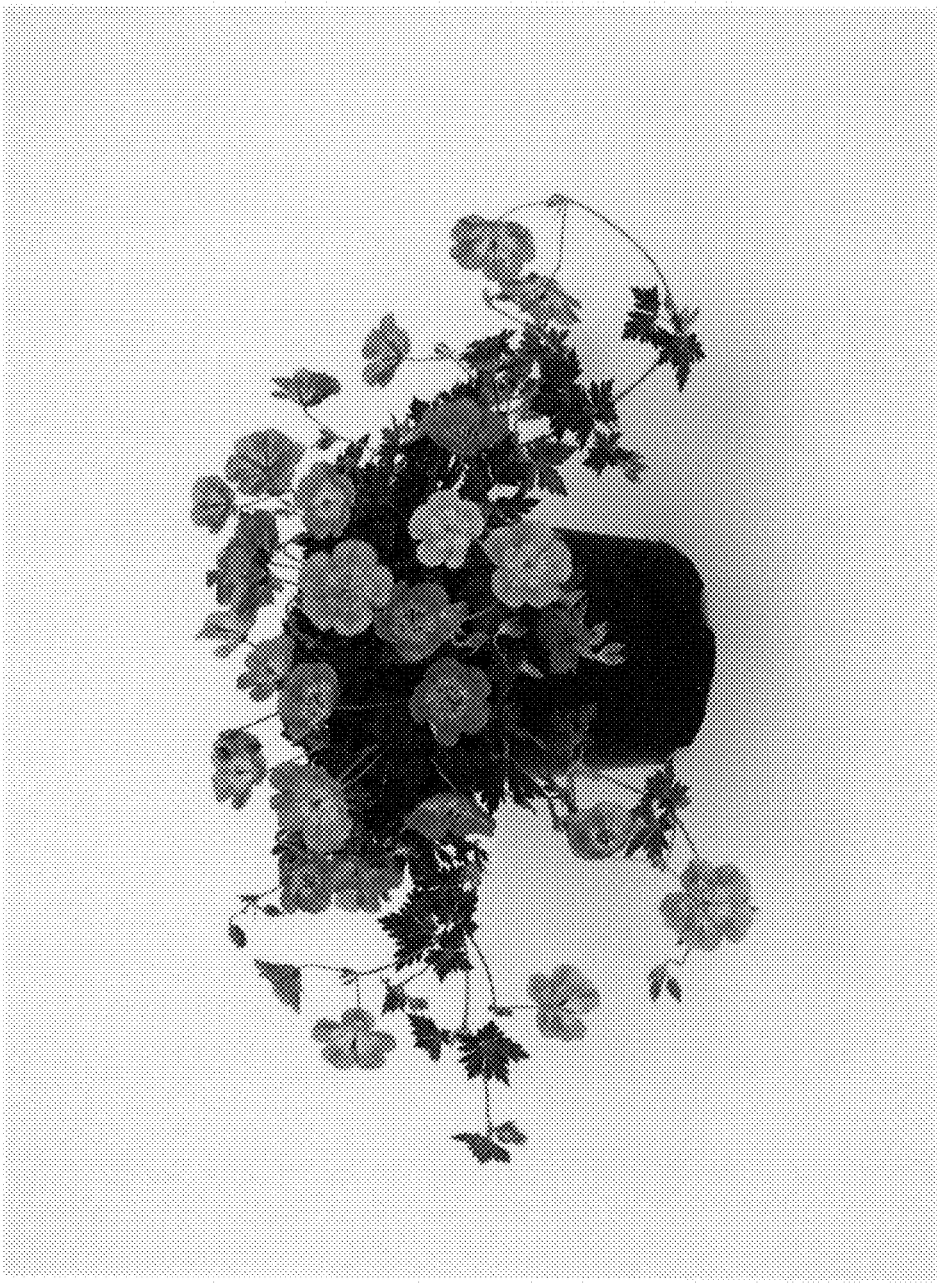

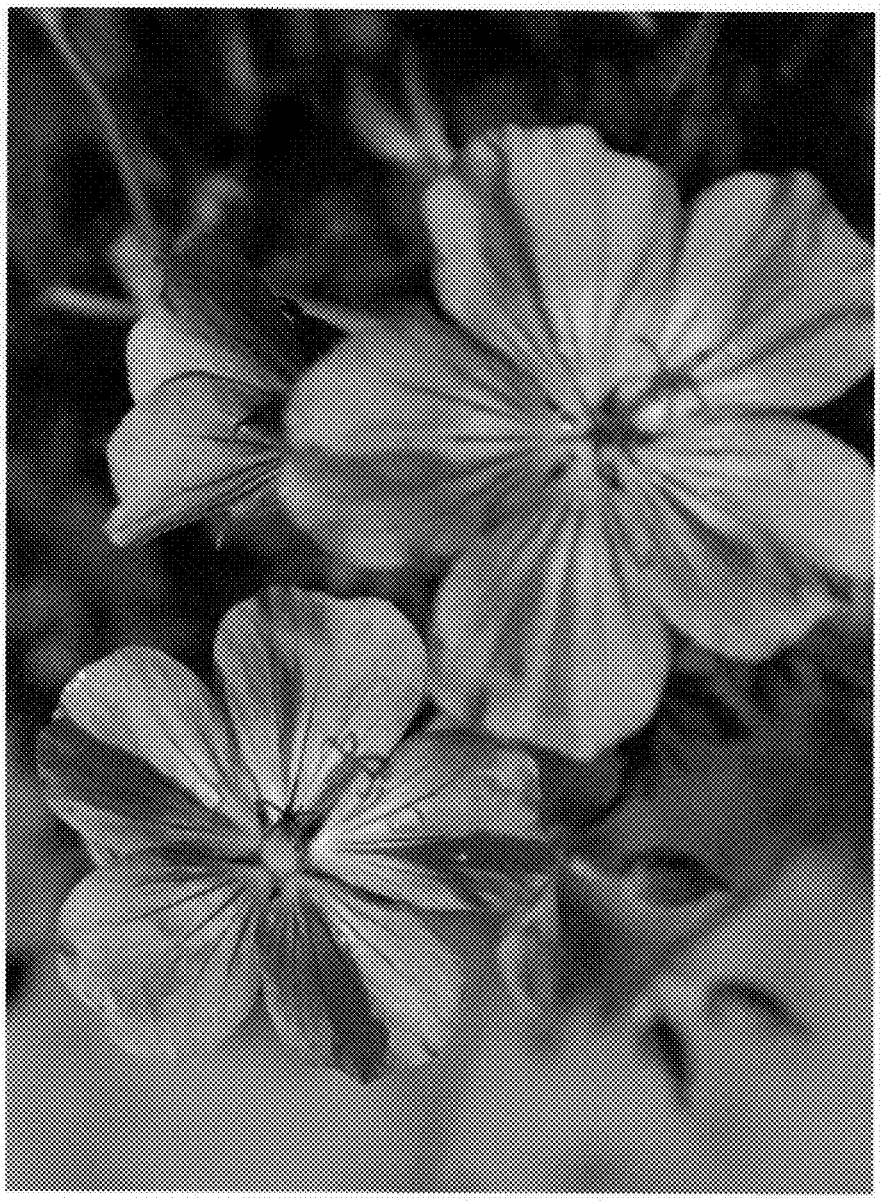

* * * * *